(12) United States Patent
Barakat et al.

(10) Patent No.: US 11,944,604 B1
(45) Date of Patent: Apr. 2, 2024

(54) NANOFORMULATION OF SPRIOOXINDOLE AND METHODS FOR TREATING HEPATOCELLULAR CARCINOMA

(71) Applicant: KING SAUD UNIVERSITY, Riyadh (SA)

(72) Inventors: Assem Barakat, Riyadh (SA); Fardous F. El-Senduny, Riyadh (SA); Mohammad Shahidul Islam, Riyadh (SA); Abdullah Mohammed Al Majid, Riyadh (SA); Yaseen Ali Mosa Mohamed Elshaier, Riyadh (SA); Eman Ahmed Ibrahim Mazyed, Riyadh (SA); Farid A. Badria, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/120,298

(22) Filed: Mar. 10, 2023

(51) Int. Cl.
| | |
|---|---|
| *A61K 31/429* | (2006.01) |
| *A61K 9/127* | (2006.01) |
| *A61K 47/26* | (2006.01) |
| *A61K 47/28* | (2006.01) |
| *A61K 47/36* | (2006.01) |

(52) U.S. Cl.
CPC .......... *A61K 31/429* (2013.01); *A61K 9/1272* (2013.01); *A61K 47/26* (2013.01); *A61K 47/28* (2013.01); *A61K 47/36* (2013.01)

(58) Field of Classification Search
None
See application file for complete search history.

(56) References Cited

U.S. PATENT DOCUMENTS

| 8,263,606 B2 | 9/2012 | Chafeev et al. |
| 8,518,984 B2 | 8/2013 | Wang et al. |
| (Continued) | | |

FOREIGN PATENT DOCUMENTS

IN 201941010579 A * 9/2020

OTHER PUBLICATIONS

ICI Americas Inc. "The HLB System a time-saving guide to emulsifier selection" ICI Americas Inc., Wilmington, Delaware, Revised Mar. 1980, pp. 1-22. (Year: 1980).*

(Continued)

*Primary Examiner* — Isaac Shomer
(74) *Attorney, Agent, or Firm* — Nath, Goldberg & Meyer; Richard C. Litman

(57) ABSTRACT

A spirooxindole nanoformulation includes a proniosome loaded with a spirooxindole derivative. In an embodiment, the spirooxindole derivative comprises (Compound 4d)

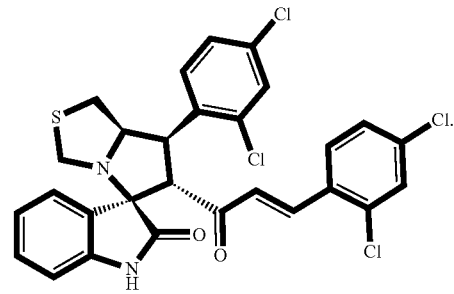

7 Claims, 6 Drawing Sheets

(56) References Cited

U.S. PATENT DOCUMENTS

| | | | |
|---|---|---|---|
| 8,859,776 B2 | 10/2014 | Bogen et al. | |
| 9,486,444 B1 | 11/2016 | Almansour et al. | |
| 9,822,128 B1 * | 11/2017 | Barakat | C07D 513/20 |
| 10,246,467 B2 | 4/2019 | Ramharter et al. | |
| 10,561,610 B2 | 2/2020 | De Beer | |
| 10,576,064 B2 | 3/2020 | Weinstabl et al. | |
| 2010/0093716 A1 | 4/2010 | Gilchrest et al. | |
| 2013/0142866 A1 * | 6/2013 | Theisinger | A61K 47/10 |
| | | | 514/625 |

OTHER PUBLICATIONS

Assem Barakat, Saeed Alshahrani et al. "Novel spirooxindole based benzimidazole scaffold: In vitro, nanoformulation and in vivo studies on anticancer and antimetastatic activity of breast adenocarcinoma." Bioorganic Chemistry, vol. 129, 2022, Article 106124, pp. 1-19. (Year: 2022).*

Uchegbu et al., "Non-ionic surfactant based vesicles (niosomes) in drug delivery," International Journal of Pharmaceutics, vol. 172, Issues 1-2, Oct. 15, 1998, pp. 33-70.

Ge et al., "Advanced of Non-Ionic Surfactant Vesicles (Niosomes) and Their Application in Drug Delivery," Pharmaceutics, 11(55), (2019).

* cited by examiner

NANOFORMULATION OF SPRIOOXINDOLE AND METHODS FOR TREATING HEPATOCELLULAR CARCINOMA

BACKGROUND

1. Field

The disclosure of the present patent application relates to novel nano-formulations of a spirooxindole derivative 4d having the structure (3R,6'S,7'R,7a'S)-7'-(2,4-dichlorophenyl)-6'-(E)-3-(2,4-dichlorophenyl)a-cryloyl)-1',6',7',7a'-tetrahydro-3'H-spiro[indoline-3,5'-pyrrolo[1,2-c]thi-azol]-2-one, and their use for treating hepatocellular carcinoma. The use of proniosomes improves the physiochemical properties of the spirooxindole derivative, providing controlled release delivery of the treating agent with enhanced efficacy.

2. Description of the Related Art

Cancer is a major cause of morbidity and mortality, affecting populations in all countries and all regions. Much recent cancer research has focused on the p53-MDM2 loop. The p53 protein, often referred to as a tumor suppressor, has been linked to transcription of proteins that mark cancer cells for cell death. Nevertheless, p53 levels that are too high may mark normal cells for cell death.

The levels of p53 in a cell are regulated by the protein MDM2. Coincidentally, the expression of MDM2 protein in the cell is the result of activation of the MDM2 gene by p53 itself. The mechanism by which MDM2 regulates p53 levels is related to the conformation of the MDM2 protein, which has folds defining a deep cleft that define a binding site for the N-terminal end of the p53 protein. Actual binding has been linked to four pairs of amino acids in p53 and MDM2 that bond to each other.

Uncontrolled growth of cancerous tumors has been correlated with elevated levels of MDM2, leading to over-suppression of p53 in at least some cancers. Consequently, one proposed strategy is to identify pharmaceutical agents that will inhibit p53-MDM2 interaction, such as by selectively binding to the site in the MDM2 protein that normally binds the p53 protein in order to elevate p53 levels.

Macromolecules and long chain proteins are not suitable because they cannot fit into the deep cleft where the binding site is located. Hence, the focus has been on small molecules. Several selective small-molecule inhibitors have been previously reported that block the MDM2-p53 protein-protein interaction and activation of p53 as a potential cancer therapeutic strategy.

The p53 protein plays an important and essential role in controlling important and related biological processes (including glycolysis, cell cycle, apoptosis, autophagy and cell differentiation). The activity of p53—often referred to as the tumor suppressor—is controlled at various stages: transcription, translation and stability.

MDM2 is E3 ubiquitin ligase, which targets p53 for proteasomal degradation. Mutated or deleted p53 protein is linked to 50% of cancer types in human. The activity of wild type p53 in cancer is inhibited by the overexpression of MDM2. Accordingly, the activation of p53 through the blocking of MDM2-p53 interaction has been an interesting and attractive target for scientists studying better treatment options for treating human carcinomas.

Spirooxindoles present unique and attractive structures that fit in the binding domain of MDM2, thereby blocking the interaction and leading to the activation and translocation of p53 to the nucleus. The nuclear translocation activates p53-target genes that are involved in the regulation of different signaling pathways.

Although some inhibitors have included spirooxindole-containing compounds, there is a need to improve the efficacy and bioavailability of MDM2 inhibitors for pharmacological use in the treatment of cancer.

Thus, an improved format for delivering substituted spirooxindoles is desired.

SUMMARY

A spirooxindole nanoformulation includes a proniosome loaded with a spirooxindole derivative. In an embodiment, the spirooxindole derivative comprises (Compound 4d)

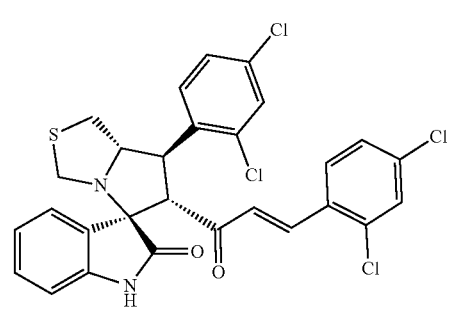

These and other features of the present subject matter will become readily apparent upon further review of the following specification.

DETAILED DESCRIPTION OF THE PREFERRED EMBODIMENTS

A spirooxindole nanoformulation includes a proniosome loaded with a spirooxindole derivative. In an embodiment, the spirooxindole derivative comprises Compound 4d

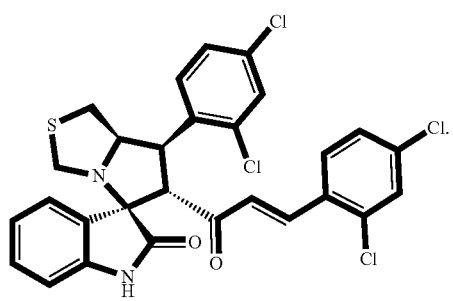

A method of treating cancer can include administering the spirooxindole nanoformulation to a patient in need thereof. In an embodiment, the cancer can be hepatocellular carcinoma. In an embodiment, the hepatocellular carcinoma can be CCl₄-induced liver cancer. The mode of action of this compound may be via activation of p53, caspase 3 and Ki-67.

The proniosomes loaded with compound 4d "herein, 4d-loaded proniosomes" can be in the form of a dry free-flowing powder that can be reconstituted at room temperature to a niosomal suspension prior to use. The 4d-loaded proniosomes can provide high entrapment efficiency in the range of 65.64±1.34 to 82.06±2.31% in vitro drug release rate up to about 12 hours. An optimized proniosomal formula ("F3", described herein) can provide significantly higher cumulative % drug release and higher stability than conventional niosomes. In experiment, the 4d-loaded proniosomes did not exhibit any chemical interactions between 4d and other excipients and displayed proper entrapment of 4d within the nanovesicles. Thus, the proniosomal formulation can provide a stable and prolonged drug delivery system.

Liposomes are phospholipid-based nanovesicles that can encapsulate both hydrophilic and lipophilic drugs. However, they have limited chemical and physical stability. Niosomes present alternate systems that may be used to overcome the limitations of liposomes. Niosomes are nanovesicles prepared using non-ionic surfactants that are more stable, and lower in cost, when compared to a system based on liposomes. However, niosomes have some physical stability problems in aqueous dispersions, such as vesicular aggregation, fusion, and leakage.

Proniosomes are prepared as either a dry, free-flowing powder in which the non-ionic surfactants are coated onto a water-soluble carrier, or as liquid crystals of surfactants with a gel-like structure. Both types of proniosomes can be readily converted to noisome suspensions prior to use through reconstitution with aqueous media. Proniosomes could overcome physical instability problems of niosomes and offer higher convenience of transportation and storage.

Figure 1:
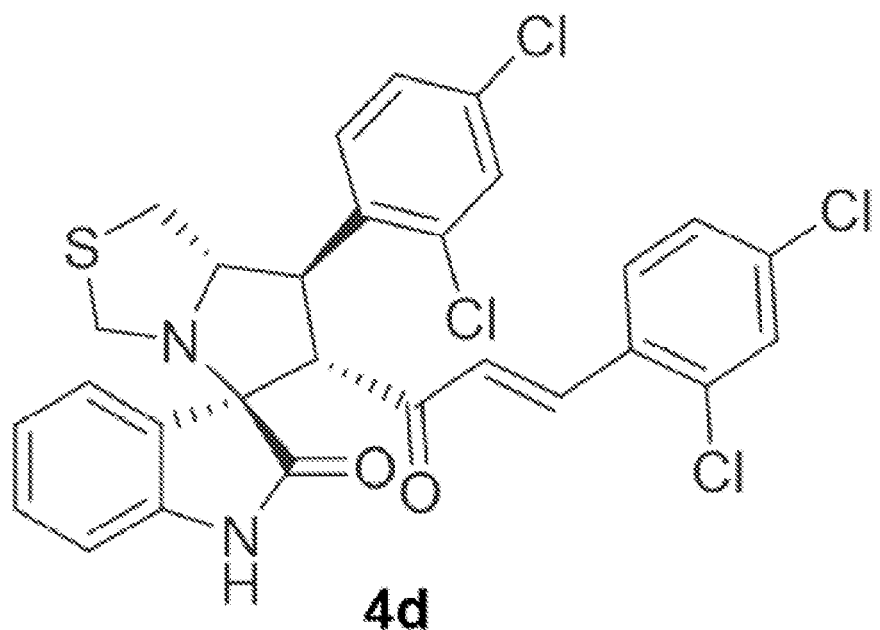
FIG. 1 depicts the structure of compound 4d: (3R,6'S,7'R,7a'S)-7'-(2,4-dichlorophenyl)-6'-((E)-3-(2,4-dichlorophenyl)acryloyl)-1',6',7',7a'-tetrahydro-3'H-spiro[indoline-3,5'-pyrrolo[1,2-c] thiazol]-2-one.

Compound 4d was disclosed along with other substituted spirooxindoles in U.S. Pat. No. 9,822,128 (FIG. 1). These compounds are MDM2-p53 inhibitors, with a benzylidene (styryl) arm and a complex fused ring system ideally suited for binding to the MDM2 protein. The compounds were generally shown to exhibit anti-cancer activity against various forms of human cancer cells. Of these compounds, compound 4d has been shown to possess a broad anticancer activity against colon, liver and prostate cancer with selectivity index greater than 2. Additionally, compound 4d led to the activation of p53 and overexpression of cell cycle inhibitor p21 gene in treated colon cancer cells, inhibited colony formation, and wound healing. Moreover, compound 4d demonstrated induction of apoptosis through the inhibition of antiapoptotic Bcl-2 and activation of Bax.

The physico-chemical properties of the target compound strongly predict the pharmacokinetics of the novel drug candidate in the drug development process. Lipophilicity is a basic physico-chemical characteristic of a chemical entity. In biological systems, lipophilicity has a major impact on both pharmacokinetics and pharmacodynamics of a novel drug candidate. Therefore, determination of lipophilicity at an early stage of development can significantly limit problems with poor absorption, distribution, metabolism, and excretion ("ADME properties") and/or improve the efficacy of novel drug candidates. The lipophilicity of a compound is typically expressed as a logarithm of partitioning coefficient.

The Rapid Overlay of Chemical Structures (ROCS) is used to perceive structural similarity between molecules based on their three-dimensional shape. Demonstrated shape similarity using the ROCS tool has different applications with regard to structural predictions. The method described herein attempts to explain the compounds' relative activity based on their 3D structures, according to common pharmacophoric features as a lead-hopping application.

Throughout this application, the term "about" may be used to indicate that a value includes the standard deviation of error for the composition, device or method being employed to determine the value.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

The following examples illustrate the present subject matter.

EXAMPLES

Materials and Methods

Figure 2:
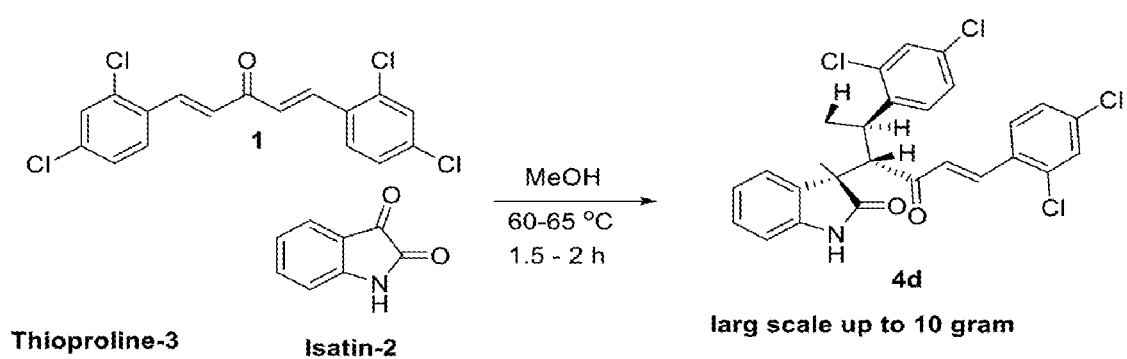
FIG. 2 depicts an exemplary reaction scheme for producing compound 4d in large scale, e.g., up to 10 grams.

The drug candidate was synthesized in a large-scale quantity for formulation and animal study according to the reaction scheme depicted in FIG. 2.

Experimental In Vivo Study

An in vivo study was carried out in Male Balb/c mice, each weighing 15-25 g. All mice were purchased from Medical Experimental Research Center (MERC), Mansoura University, Egypt. Mice were acclimatized for one week in the new animal care facility, at the Zoology Department, Mansoura University, Egypt, under specific pathogen-free (SPF) conditions, and provided with conventional food and drinking water before the study. All animal experiments were carried out following the guidelines of the faculty of Science, Mansoura University, Egypt.

The lethal dose of compound 4d was evaluated according to standard Dose-Probing Tests. Mice were divided into groups of three for evaluating the LD50. Each group received either a different concentration of compound 4d (ranging from 10 ng/Kg to 200 mg/Kg), in corn oil, or the solvent 10% DMSO in corn oil, by intraperitoneal (IP) injection.

The weight and physical symptoms of the mice were monitored for 14 days. After that, all groups were sacrificed, and the liver, kidney, heart, and spleen were collected for histological evaluation of the toxicity of compound 4d. Blood was collected from each mouse for evaluation of the effect of compound 4d on liver and kidney function.

Twenty five mice were treated with carbon tetrachloride ($CCl_4$, from LOBA Chemie Pvt Ltd, Mumbai, India, 1:5 in corn oil) twice weekly via IP injection for 24 weeks. After that period of time, mice were distributed evenly into 5 groups of 5 mice. Group 1 was treated with the solvent 10% DMSO; group 2 was treated with a low dose of compound 4d (50 mg/kg/daily) for 14 days; group 3 was treated with a high dose of compound 4d (200 mg/kg) for 6 hours; group 4 was treated with a high dose of compound 4d (200 mg/kg) for 24 hours; and group 5 was treated with a high dose of compound 4d (200 mg/kg) for 48 hours.

At the end of each treatment, all mice were sacrificed, and blood and liver were collected for evaluation. The liver samples were washed in ice cold 1× phosphate buffered saline (PBS), and fixed in 10% buffered formalin till examination.

The blood was centrifuged to collect serum or plasma for biochemical analysis. The blood chemistry was evaluated to detect the level of serum alanine aminotransferase (ALT), serum aspartate aminotransferase (liver function test), and serum creatinine (kidney function test). Complete blood count analysis was carried out to detect the effect of compound 4d treatment on blood platelet count, because it has been reported that p53-MDM2 inhibitors cause high grade thrombocytopenia (i.e., decreased numbers of platelets).

The formalin-fixed liver specimens were embedded in paraffin, and sections were taken and prepared for hematoxylin and Eosin (H&E) staining. The slides were examined for hepatic architecture, degenerative changes, inflammatory changes, hepatocytes necrosis, mitosis, dysplastic changes and malignant transformation. 4 μm thick sections were prepared on coated slides.

The sections were de-paraffinized in xylene, then rehydrated. Endogenous tissue peroxidase was blocked by incubating the slides for 5 minutes in 0.3% hydrogen peroxide. Antigen retrieval was done by heating the sections in citrate buffer, at pH 6.0, in a microwave. Then, the sections were incubated with monoclonal mouse p53 (clone DO-7, Dako, USA), rabbit polyclonal caspase 3 antibody (CPP32) Ab-4 (ThermoScientific), or with monoclonal mouse Ki-67 antigen (clone MIB-1, Dako, USA).

The slides were counterstained with hematoxylin and then dehydrated in alcohol and cleared xylene. The immunohistochemical and pathological changes were examined by light microscopy (binocular, Olympus). Images were taken using a digital camera (Canon, 5 mega pixels, at 3.2× optical zoom). A total of 10 fields per section were randomly selected and examined.

Statistical Analysis

The statistical analysis was done using the software SPSS 19 for Microsoft Windows (SPSS Inc, Chicago, Illinois). A quantitative analysis of the number of hepatocytes with positive nuclear Ki-67 staining were tested using a one-way analysis of variance (ANOVA), with Duncan's multiple comparisons of the means to compare difference between means.

The statistical data were expressed as means±standard errors. The difference between means was considered significant when ($P<0.05$). The data of blood chemistry and CBC were expressed as means±standard deviation (SD). The differences between multiple groups were compared by t-test; results with P value less than 0.05 were considered statistically significant.

ROCS Study

A receiver operating characteristic curve analysis (ROCS) was performed using ROCs application OpenEye scientific software. Compound 4d was selected as the query molecule, and a compound library of spirooxindoles was adopted as the database file.

A ROCS graphical editor was employed to run and analyze/visualize the results. The ROCS application searched the database with the query to find molecules with similar shape and colors. Compounds conformers were scored based upon the Gaussian overlap to the query, and the best scoring parameters is Tanimoto Combo scores (shape+color). The highest score is the best match with the query compound.

Formulation of 4d-Loaded Proniosomes

A preliminary screening study was done to choose the most appropriate formulation parameters. The dry proniosomes were hydrated before administration, to be converted to the niosomal dispersion. Short hydration time and hydration at room temperature would increase the applicability of the formulation and patient compliance.

In order to choose the proper surfactant and the appropriate hydration time, the proniosomal formulations were prepared using 5 mg/ml of compound 4d, in maltodextrin as the carrier, and a 140:60 pmolar ratio of surfactant to cholesterol (CHOL). The hydrophilic carrier and the molar ratio of surfactant to CHOL were chosen randomly. The first step of the prescreening test was choosing the surfactant that could formulate proniosomes that are rehydrated at 25° C.

Two surfactants (Span 80 and Span 60) were employed for the preparation of 4d-loaded proniosomes. The proniosomal formulations were tested for vesicle formation at 25° C. using optical microscope (Coslabs micro, India).

The next step was studying the proper time of hydration of the proniosomal powder. Three different hydration times (2, 5 and 30 min) were investigated for hydration of the selected proniosomes by measurement of entrapment efficiencies (EE %).

Example 1

Fabrication of 4d-Loaded Proniosomes Using the Slurry Method

Proniosomes of 4d compound were formulated by the slurry method. Accurately weighed amounts of 4d (5 mg/ml), non-ionic surfactant, and CHOL were dissolved in 10 ml chloroform. The slurry was formed by introducing the resultant solution into a round-bottom flask containing the hydrophilic carrier.

The organic solvent was removed at 60±2° C. under reduced pressure (16 mm Hg) using a rotary evaporator (Buchi rotavapor R-3000, Switzerland) that was adjusted to 80 rpm until the mass in the round-bottom flask became a completely dry, free-flowing product. The formulated proniosomes were stored in a desiccator to be used for further studies.

Example 2

Experimental Design of Proniosomes of 4d Using $2^3$ Factorial Design

Proniosomes of 4d were fabricated according to a two-level ($2^3$) factorial design using Design-Expert software, Version 7 (Stat-Ease Inc., Minneapolis, MN, USA) to explore the impact of different formulation variables on the characteristics of different proniosomal vesicles. In this design, the type of carrier (X1), the ratio of Span 80 to CHOL (X2), and the volume of hydration (X3) were selected as independent factors. Each variable was screened at three levels: the lower, the middle, and the upper levels (−1, 0 and +1), respectively. The percentage of drug released after 12 h ($Q_{12h}$, Y1) and entrapment efficiency (EE %, Y2) were selected as the responses.

The degree of fit of the model to the experimental data was tested by determination of the coefficient of determination ($R^2$), adjusted $R^2$, and predicted $R^2$ that are considered statistical measures of closeness of the data to the fitted regression line. Analysis of variance (ANOVA) was used for statistical analysis, and for determining the statistical significance of the obtained results on the basis of F statistics and the P-value.

The P-value was used to check the significance of each coefficient. A P-value that is lower than 0.05 was considered to be significant at a level of significance $\alpha$=0.05, showing that the corresponding factor is significant and the null hypothesis could be rejected. The smaller the P-value, the more significant the tested coefficient.

Example 3

Preparation of proniosome-derived niosomal dispersions of 4d

The niosomal dispersion of 4d was prepared by hydration of the proniosomal powder using distilled water at 25° C.±2° C. for 3 min using a vortex mixer (BOECO, Germany). The niosomal dispersion was then sonicated using a bath sonicator (Elmasonic E 30 H, Elma, Singen, Germany) for 5 min and left in a refrigerator at 4° C. to mature overnight to be used for further studies.

Example 4

Determination of Drug Content and Entrapment Efficiency of 4d-Loaded Proniosomes The EE % of proniosome-derived niosomal dispersions of 4d was determined using the indirect method. The ultracentrifugation method was used for separation of the free (unentrapped) drug using a cooling ultracentrifuge (Biofuge, primo Heraeus, Germany) at 14,000 rpm for 1 hr at 4° C. The supernatant was separated and analyzed for drug content. Encapsulation efficiency was calculated as follows:

$$EE(\%) = (A1 - A2) \times 100 / A1$$

where A1=Initial amount of drug, A2=Amount of drug in the supernatant.

For the determination of total drug content (unentrapped+ entrapped), 1 ml of proniosome-derived niosomal dispersion was disrupted by isopropyl alcohol (100 ml). The samples were filtered through a 0.45 μm membrane filter and analyzed for drug content.

Example 5

In Vitro Release of 4d-Loaded Proniosomes

In vitro release of proniosome-derived niosomal dispersions of 4d was studied using modified Franz diffusion cells. The cellulose membrane was hydrated using a phosphate buffer solution at pH of 7.4 for 24 hours at room temperature.

The hydrated cellulose membrane was mounted precisely between the donor and receptor compartments. The receptor medium was 20 ml phosphate buffer solution (pH 7.4) containing 1% sodium lauryl sulfate (SLS) to maintain sink conditions. The receptor compartment was kept at 37±0.5° C. and stirred at 100 rpm using a magnetic stirrer.

An accurate volume (1 ml) of the proniosome-derived niosomal dispersions containing entrapped 4d was placed over the cellulose membrane in the donor compartment. 200 μl samples were taken at predetermined time intervals, and the receiver cell was replenished with an equal volume of fresh phosphate buffer solution. The withdrawn samples were analyzed for drug content. Triplicate measurements were done for each study, and the data were expressed as the mean values±SD.

The mechanism of in vitro release of 4d-loaded proniosomes was explored by studying the release kinetics through treating the data of drug release using different mathematical models. The model having the highest coefficient of determination ($R^2$) was selected to describe the in vitro release profile.

Example 6

Statistical Optimization of 4d-Loaded Proniosomes

Selection of the optimized 4d-loaded proniosomal formula depends on determination of the desirability index that describes the desirable range for each response. The value of desirability index lies between 0 and 1. The value 0 corresponds to an undesirable response, while the value 1 expresses an optimal performance of the studied factors. In the present model, the choice of the optimized proniosomal formula depends on maximizing both $Q_{12h}$ and EE %. The optimized 4d-loaded proniosomal formula was evaluated by further characterization tests.

Example 7

Comparative Study of the Optimized Proniosomal Formula and the Conventional Niosomes A comparative study was performed between the optimized proniosomal formula and the corresponding niosomal dispersion through evaluation of EE %, $Q_{12h}$ and stability study.

Example 8

Formulation of Compound 4d-Loaded Niosomes

Compound 4d-loaded niosomes were formulated using thin film hydration method. Briefly, compound 4d (5 mg/ml), Span 80 and CHOL were mixed at the selected molar concentrations and dissolved in 10 ml chloroform in a round bottom flask. The organic solvent was then removed under vacuum in a rotary evaporator at 60±2° C. under reduced pressure (16 mm Hg) using a rotary evaporator (Buchi rotavapor R-3000, Switzerland) leaving a thin lipid film on the walls of the flask. The thin lipid film was rehydrated by 10 ml phosphate buffer (pH 7.4) and rotated for 30 min at 60±2° C. The resultant niosomal dispersion was left to mature overnight and stored in a refrigerator at 4° C. for further characterization.

Example 9

Evaluation of EE % and In Vitro Release of 4d-Loaded Niosomes

The EE % and the in vitro release profile of 4d-loaded niosomes were studied as previously described. The in vitro release profile of the 4d-loaded niosomes was compared to that of the optimized proniosomal formula according to the similarity factor test in which the in vitro release profiles are declared similar if the value of f2 is between 50 and 100. f2 is calculated according to the following equation:

$$F2 = 50 \cdot \log\left\{\left[1 + \frac{1}{n}\sum_{t=1}^{n}(R_t - T_t)^2\right]^{-0.5}\right\}100$$

Where Rt and Tt are the % drug released at time t from the optimized 4d-loaded proniosomal formula and the corresponding niosomes, respectively, and n is the number of sampling points.

Example 10

Stability Study of Optimized 4d-Loaded Proniosomal Formula and the Corresponding Niosomes Stability testing is a critical parameter that describes the effect of storage on the stability and characteristics of the formulation. Both the 4d-loaded proniosomal formula and the corresponding niosomes were kept in tightly closed containers and stored in a refrigerator at 4° C. for a period of 3 months. The residual drug content and EE % of the stored formulations were evaluated at predetermined time intervals as a measure of the stability of the nanovesicles.

Example 11

Evaluation of the Selected Formula of 4d-Loaded Proniosomes

The optimized 4d-loaded proniosomal formula was characterized by evaluation of the micromeritic properties, Fourier-transform infrared spectroscopy (FTIR), differential scanning calorimetry (DSC), morphological examination and determination of vesicle size and zeta potential.

Micromeritic Properties

The flow properties of the selected proniosomal powder were determined by measurement of the angle of repose of both the carrier and the optimized proniosomal powder by the funnel method. The carrier or proniosome powder was poured through a funnel that was fixed at a certain height so that the outlet orifice of the funnel is 5 cm above a graph paper surface. The powder flowed down from the funnel forming a cone on the paper surface. The angle of repose was then determined by measuring the height of the powder pile (h) and the radius (r) of its base. The angle of repose was calculated as follows:

$$\text{Tan } \theta = h/r$$

Where $\theta$ is the angle of repose; h is the height of the powder pile; r is the radius of the base.

Scanning electron microscopy (SEM)

The morphological features of the reconstituted proniosomal formula were examined by scanning electron microscope (SEM) (Jeol, JSM-6360, Japan). The diluted dispersion was mounted onto the aluminum stub using double-sided sticky carbon tape, and dried under reduced pressure. The sample was subsequently coated with gold film. The coated specimen was examined and photographed by SEM.

Vesicle Size and Zeta Potential Determination

The vesicle size and zeta potential were determined for investigating the colloidal features of the reconstituted proniosomal formula. The reconstituted proniosomal formula was suitably diluted by distilled water. Then, a NICOMP 380 ZLS zeta potential/particle size (PSS Nicomp, Santa Barbara, CA, USA) was used for estimation of vesicle size and zeta potential. The average of three measurements was recorded.

Fourier Transform Infrared Spectroscopy (FTIR)

Potential interactions between the compound 4d and different additives were studied by FT-IR using the FT-IR spectrometer (FTIR Shimadzu 8300 Japan). Samples of 4d, different excipients, plain proniosomes and the optimized 4d-loaded proniosomal formula were used. All samples were ground and mixed with potassium bromide to form pellets in a hydraulic press (Kimaya Engineers, Maharastra, India). The spectral range of the pellets was 4000-400 cm$^{-1}$.

Differential Scanning Calorimetry (DSC) Study

DSC was used to study the change in the crystalline state of 4d in the optimized proniosomal formula using a Shimadzu DSC 60 (Japan, Kyoto). The samples of 4d, plain proniosomes and the chosen 4d proniosomal formula were heated in aluminum pans in the range of 20-260° C. with a heating rate of 10° C./min, and the DSC thermograms were recorded.

Example 12

Compound 4d Safety and Efficacy Studies

In order to evaluate the tolerated dose of compound 4d, mice were intraperitoneally injected with different doses, and physical symptoms were evaluated daily for 14 days. The maximum dose used was 200 mg/kg, because of the solubility limitation in DMSO. DMSO was adjusted to the tolerated dose 10% in corn oil.

Compound 4d did not cause any change in the behavior, feeding or drinking of the mice. The complete blood count showed that there is no aberrant or significant change in the platelet count (Table 1). Additionally, the effect of compound 4d treatment on liver and kidney function was evaluated by measuring the level of aspartate aminotransferase (AST), alanine aminotransferase (ALT) and serum creatinine, respectively. The analysis revealed that AST, ALT and creatinine level was not changed by compound 4d treatment (Table 1). This finding of the safety of compound 4d on healthy mice was confirmed by histopathology analysis for fixed liver, heart, kidney and spleen specimens to examine hepatic architecture, degenerative changes, inflammatory changes, hepatocytes necrosis, mitosis, dysplastic changes and malignant transformation. Hematoxylin and eosin staining showed normal liver architecture without any degenerative changes after compound 4d treatment for 14 days. Moreover, compound 4d did not cause any pathological alteration in kidney, heart or spleen. These data confirm the applicability and safety of compound 4d.

Moreover, compound 4d did not cause any pathological alteration in kidney, heart or spleen. These data confirm the applicability and safety of compound 4d.

Compound 4d Improved the Liver Histopathology

Figure 3A:
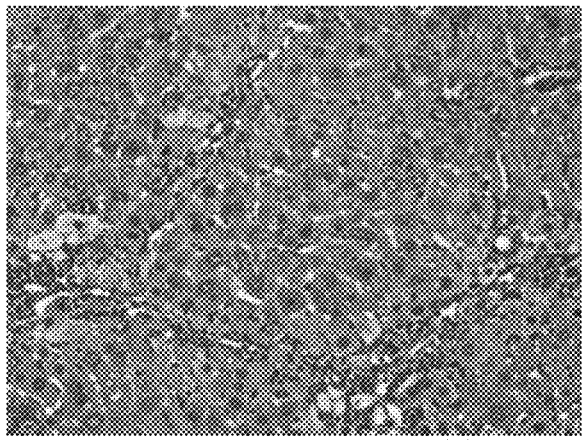
FIG. 3A depicts an H&E liver staining showing $CCl_4$-treated mice with large cell dysplasia (premalignant development).

An in vivo model was carried out to test the efficacy of compound 4d in treatment of liver cancer by applying two regimens of compound 4d: a single dose of 200 mg/kg and the treated mice were sacrificed after 6, 24 or 48 hours; or a daily dose of 50 mg/kg for 14 days. Liver cancer was induced chemically by $CCl_4$ (1:5 dilution in corn oil, twice per week). H&E slides for $CCl_4$-treated mice showed large cell dysplasia (premalignant). The liver architecture was disturbed and there were cirrhotic nodules with bridging fibrosis (FIG. 3A).

The liver cells showed piecemeal necrosis (interface hepatitis). The liver cells also showed vacuolar degeneration with enlarged cytoplasm and nuclei with variability in size. The mitotic activity was high (12 mitotic figure/10 high power field (H.P.F.) with high level of inflammatory infiltration in both portal tracts and parenchyma due to the accumulation of leukocytes.

H&E slides for the daily dose of 50 mg/kg compound 4d-treated group showed multiple liver lobes with confluent liver cell necrosis and excess inflammatory cellular infiltrate. However, other areas showed preserved liver architecture with mild inflammatory cellular infiltrate in portal tracts. Moreover, the liver cells showed no nuclear changes and no mitotic activity, indicating the ability of compound 4d to treat or stop the progression of hepatic cancer. This improvement in liver architecture was significantly reflected on the serum level of liver enzymes AST (P=<0.001) and ALT (P=<0.001) in comparison to DMSO-treated mice. See Table 2.

TABLE 1

No alteration in hemoglobin, platelets or leukocyte count after treatment of mice with compound 4 d. Statistical analysis showed differences were not significant (P value > 0.05).

| Parameters | DMSO[a] | 50 mg/kg/ 14 d[b] | 200 mg/kg/ 24 hrs[c] | 200 mg/kg/ 48 hrs[d] | P |
|---|---|---|---|---|---|
| Hb | 11.7 ± 1.6 | 10.16 ± 1.1 | 10.1 ± 1.43 | 10.4 ± 1.78 | a vs b = 0.133 |
| | | | | | a vs c = 0.122 |
| | | | | | a vs d = 0.260 |
| Platelets | 749.2 ± 424.9 | 433.0 ± 304.6 | 519 ± 302.9 | 407.0 ± 281.6 | a vs b = 0.199 |
| | | | | | a vs c = 0.228 |
| | | | | | a vs d = 0.159 |
| Leukocytes | 15.7 ± 5.2 | 12.5 ± 6.9 | 10.6 ± 6.9 | 13.6 ± 6.4 | a vs b = 0.403 |
| | | | | | a vs c = 0.195 |
| | | | | | a vs d = 0.567 |
| GOT | 308.3 ± 191.1 | 281.0 ± 231.9 | 129.6 ± 56.5 | 145.7 ± 198.9 | a vs b = 0.835 |
| | | | | | a vs c = 0.072 |
| | | | | | a vs d = 0.201 |
| GPT | 653.7 ± 193.2 | 486.6 ± 339.9 | 498.0 ± 228.8 | 368.0 ± 208.1 | a vs b = 0.331 |
| | | | | | a vs c = 0.252 |
| | | | | | a vs d = 0.167 |
| Creatinine | 0.689 ± 0.5 | 0.49 ± 0.21 | 0.67 ± 0.24 | 0.692 ± 0.567 | a vs b = 0.421 |
| | | | | | a vs c = 0.975 |
| | | | | | a vs d = 0.953 |

TABLE 2

Biochemical markers of liver function (mean ± SD) improved after compound 4d treatment for 24 or 48 hours without any side effect on kidney.

| Parameters | $CCl_4{}^a$ | $CCl_4$ + 50 mg/kg/14 d$^b$ | $CCl_4$ + 200 mg/kg/6 hrs$^c$ | $CCl_4$ + 200 mg/kg/24 hrs$^d$ | $CCl_4$ + 200 mg/kg/48 hrs$^e$ | P |
|---|---|---|---|---|---|---|
| GOT (AST) | 3667.0 ± 120.1 | 449.20 ± 109.2 | 3419.00 ± 130.5 | 1161.00 ± 108.5 | 208.40 ± 9.32 | a vs b = <0.001<br>a vs c = 0.014<br>a vs d = <0.001<br>a vs e = <0.001 |
| GPT (ALT) | 3628.0 ± 342.1 | 2028.6 ± 168 | 3430.4 ± 137.48 | 2209.0 ± 132.8 | 961.6 ± 15.96 | a vs b = <0.001<br>a vs c = 0.282<br>a vs d = <0.001<br>a vs e = <0.001 |
| Creatinine | 0.4240 ± 0.21 | 0.4120 ± 0.2 | 0.4560 ± 0.18229 | 0.4860 ± 0.17 | 0.4660 ± 0.16 | a vs b = 0.929<br>a vs c = 0.803<br>a vs d = 0.624<br>a vs e = 0.733 |

The application of a single dose regimen have been used by two scientific research groups. See Gollner A, Rudolph D, Arnhof H, et al. Discovery of Novel Spiro [3H-indole-3,2'-pyrrolidin]-2(1H)-one Compounds as Chemically Stable and Orally Active Inhibitors of the MDM2-p53 Interaction, *Journal of Medicinal Chemistry* 59(22):10147-10162 (2016); and Wang S, Sun W, Zhao Y, et al. SAR405838: An Optimized Inhibitor of MDM2-p53 Interaction That Induces Complete and Durable Tumor Regression, Cancer Research 74(20):5855-5865 (2014).

Figure 3B:
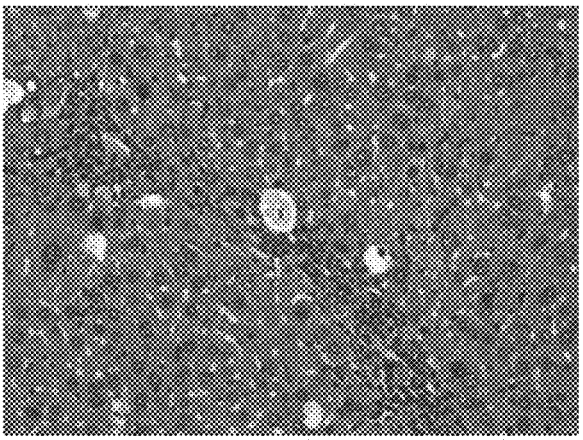
FIG. 3B depicts an H&E liver staining showing $CCl_4$-treated mice further treated with one dose of 200 mg/kg compound 4d, after 6 hours.

As noted above, compound 4d efficacy was student when administered at a single dose of 200 mg/kg for different time points (6, 24 or 48 hours). After 6 hours, the same histopathological pattern of the liver prepared from mice treated with $CCl_4$ was observed where photomicrograph showed bridging fibrosis, high inflammatory infiltrate, and anisonucleosis (i.e., nuclei vary in size) with minimal mitotic activity (1/10 H.P.F.) indicating that this single high dose of compound 4d inhibited mitosis (FIG. 3B).

Figure 3C:
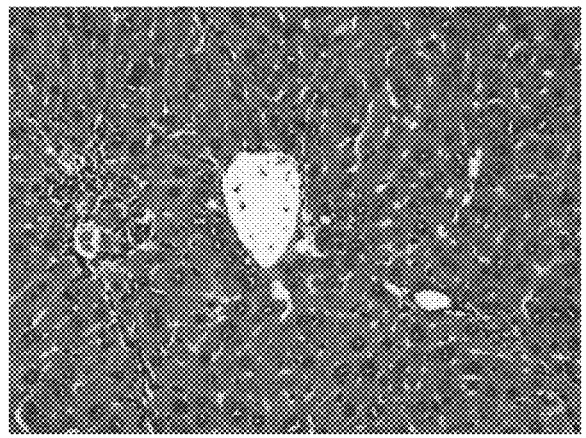
FIG. 3C depicts an H&E liver staining showing $CCl_4$-treated mice further treated with one dose of 200 mg/kg compound 4d, after 24 hours.
Figure 3D:
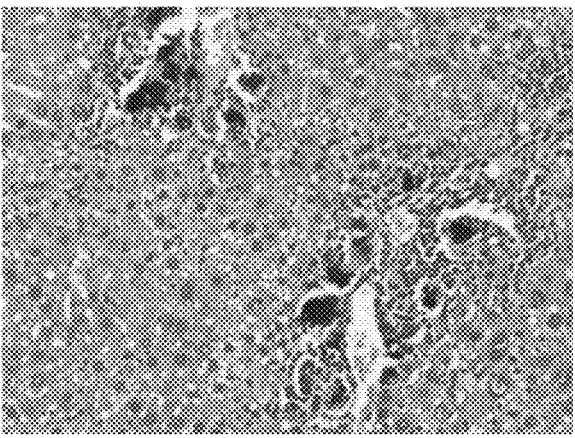
FIG. 3D depicts an H&E liver staining showing $CCl_4$-treated mice further treated with one dose of 200 mg/kg compound 4d, after 48 hours.

Longer incubation with the single dose showed a different pattern of liver architecture, where the sections revealed some cirrhotic nodules, but there was mild inflammatory cellular infiltrate in portal tracts and the nuclei showed minimal anisonucleosis and lower mitotic activity (1/10 H.P.F.). The liver of mice treated for 24 hours showed mild inflammatory cellular infiltrate in portal tracts, and the nuclei showed minimal anisonucleosis, and lower mitotic activity (FIG. 3C). The liver of mice treated for two days showed cirrhotic nodules with bridging fibrosis and intense inflammatory cellular infiltrate in portal tracts. The liver cells showed microvascular steatosis with numerous calcification foci in the portal tracts (FIG. 3D) The mitotic activity was low (2/10 H.P.F.) The finding results from single dose confirm the ability and efficacy of compound 4d in treating liver and histopathological results was in accordance with significant lower level of serum ALT (p=<0.001) and AST (p=<0.001) of the treated groups (Table 2).

Example 13

Activation of p53 by Compound 4d

In order to evaluate the effect of compound 4d on the activation of p53 in an animal model, mice were treated and then immunohistochemistry analysis was performed to detect the level of p53 in the fixed liver sections. The compound 4d treatment at both tested regimen —low or high dose—was able to activate p53. Mice treated with $CCl_4$ and further treated with low dose 4d for 14 days, or with high dose 4d for 6, 24, or 48 hours, showed time-dependent activation of p53 (FIGS. 4A and 4B and FIGS. 5A to 5D, respectively).

Figure 4A:
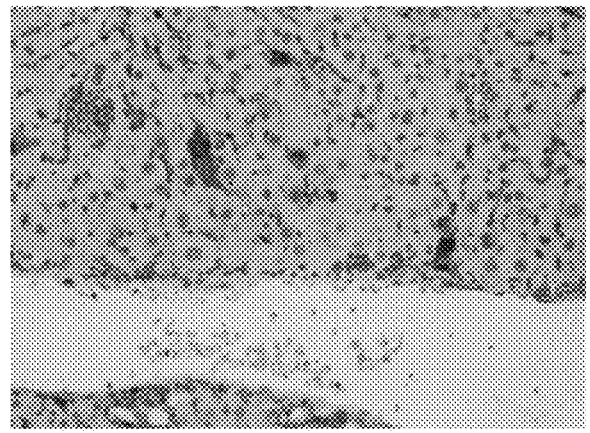
FIG. 4A depicts a stained mouse liver section, for mice treated with $CCl_4$ and showing low level p53.
Figure 4B:
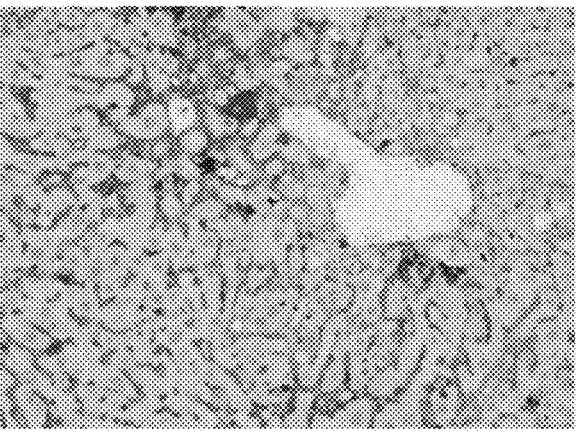
FIG. 4B depicts a stained mouse liver section, for mice treated with $CCl_4$ and then 50 mg/kg daily for 14 days.
Figure 5A:
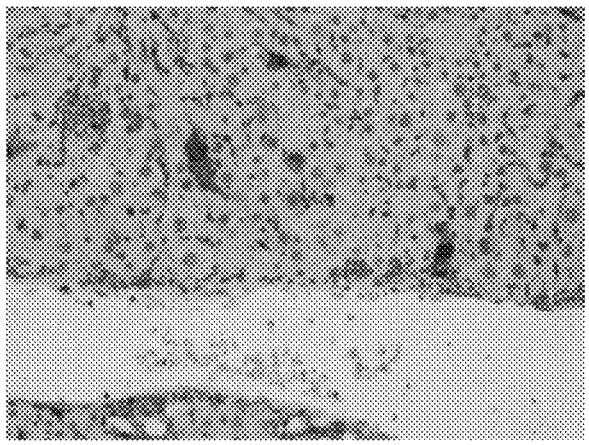
FIG. 5A depicts a stained mouse liver slide, for mice treated with $CCl_4$ and showing low level p53.
Figure 5B:
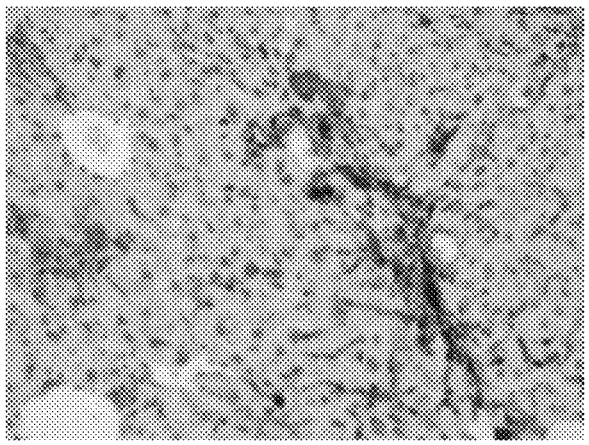
FIG. 5B depicts a stained mouse liver section, for mice treated with $CCl_4$ and then a single dose of 200 mg/kg for 6 hours.
Figure 5C:
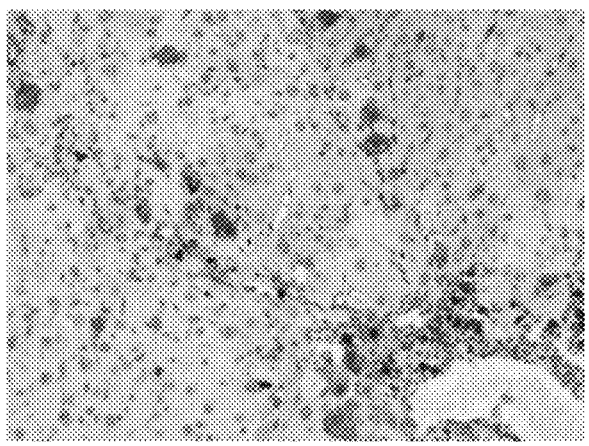
FIG. 5C depicts a stained mouse liver section, for mice treated with $CCl_4$ and then a single dose of 200 mg/kg for 24 hours.
Figure 5D:
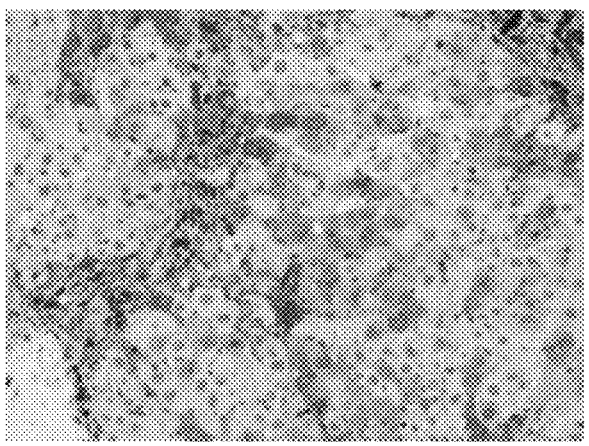
FIG. 5D depicts a stained mouse liver section, for mice treated with CCl₄ and then a single dose of 200 mg/kg for 48 hours.

The mice treated with a daily dose of 50 mg/kg for 14 days showed higher levels of detected p53 in liver sections than mice only treated with the $CCl_4$ (FIGS. 4B and 4A). Similarly, mice treated with a single dose of 200 mg/kg for 6, 24 or 48 hours showed time-dependent activation of p53 (FIGS. 5A to 5D).

These results confirmed the efficacy of compound 4d in treating liver cancer.

Example 14

Compound 4d Induces Apoptosis p53 is a tumor suppressor, and its activation either led to the DNA repair or induction of apoptosis if the DNA damage is extensive. In order to confirm the transactivation of p53 in $CCl_4$-treated mice after injection of compound 4d, the level of apoptotic executioner caspase 3 was detected.

Figure 6A:
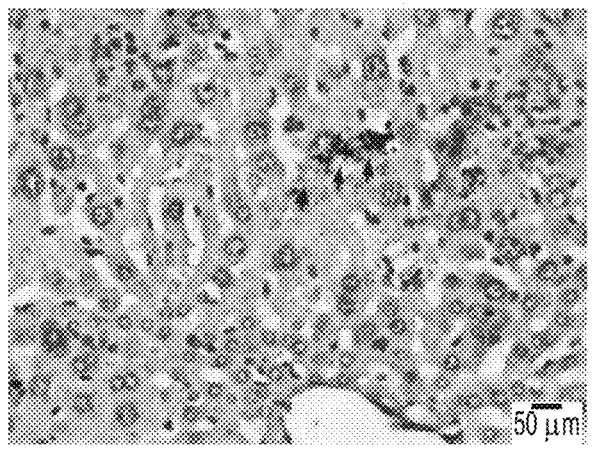
FIG. 6A depicts normal level of caspase 3 in healthy mice.
Figure 6B:
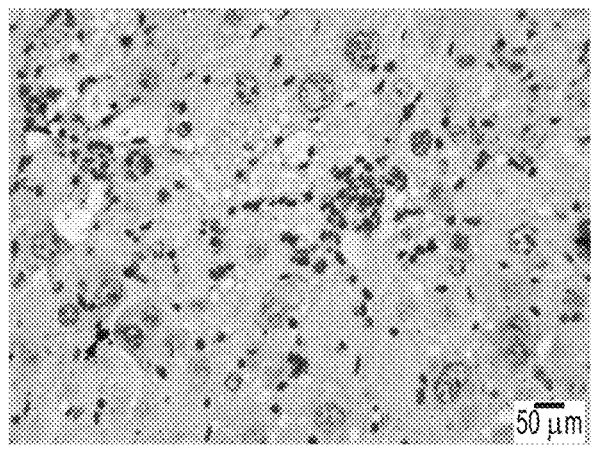
FIG. 6B depicts very low level of caspase 3 in CCl₄-treated mice.
Figure 6C:
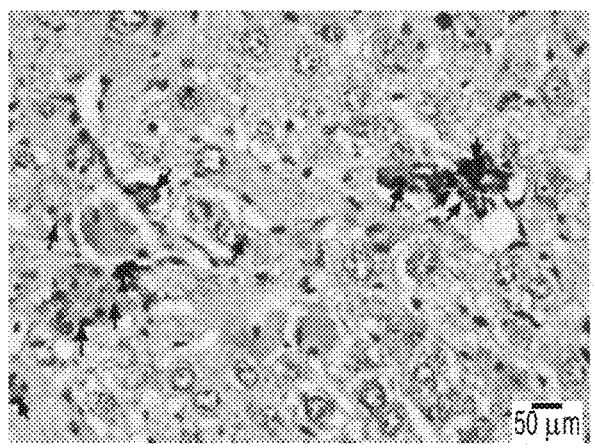
FIG. 6C depicts activation of caspase 3 in CCl₄-treated mice after further treatment with 50 mg/kg compound 4d daily for 14 days.
Figure 6D:
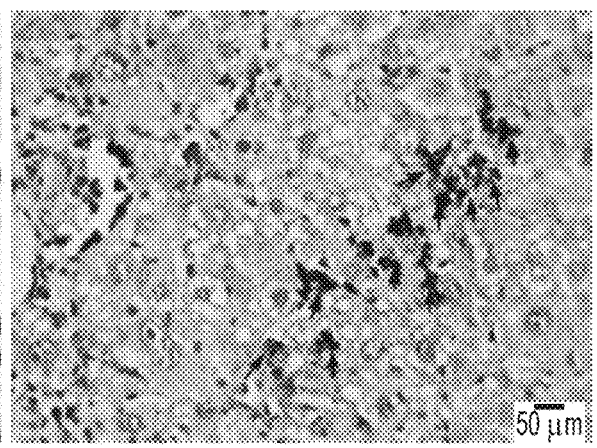
FIG. 6D depicts activation of caspase 3 in CCl₄-treated mice after further treatment with 200 mg/kg compound 4d for 48 hours.

The liver sections were immuno-stained with caspase 3, and the level of staining was examined by bright microscope. As depicted in FIG. 6A, healthy mice showed normal Levels of caspase 3 (black arrows). In contrast, $CCl_4$-treated mice showed very low level of caspase 3 (FIG. 6B). Further, treating the $CCl_4$ mice with compound 4d, whether at low dose daily for 14 days or at high dose for 48 hours, induced the activation of caspase 3, confirming the ability of compound 4d to activate p53 (FIGS. 6C and 6D, respectively).

Example 15

Compound 4d Induces Liver Cell Regeneration

Induction of apoptosis in liver cells leads to liver damage and increase the level of enzymes such as ALT and AST. Interestingly, during this study, the level of the two enzymes was decreased close to the normal level in healthy mice, suggesting that compound 4d induces liver regeneration after $CCl_4$-inducing damage.

The level of proliferative Ki-67 marker was evaluated using immunohistochemistry. Ki-67 detection in hepatocytes was examined.

Figure 7:
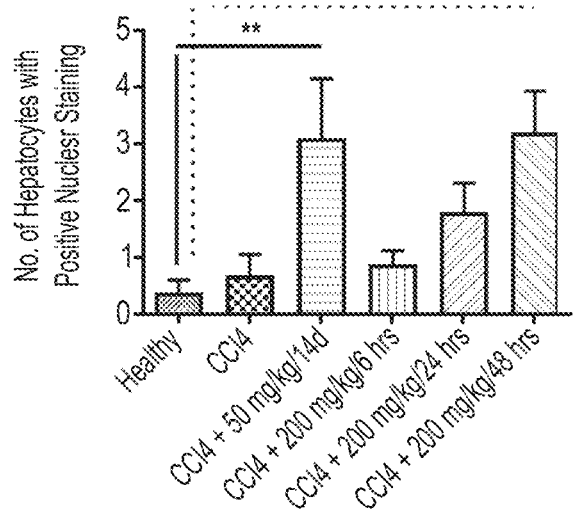
FIG. 7 depicts a significant increase in Ki-67 nuclear staining in mouse hepatocytes after treatment with compound 4d.

FIG. 7 shows that healthy mice did not show any hepatocyte KI-67 staining while few hepatocytes were stained (black arrow) with Ki-67 in $CCl_4$-treated group. Treatment of $CCl_4$-induced liver damage and treatment of mice with compound 4d either with low (daily dose for 14 days) or high dose (single dose) significantly increased the number of Ki-67 nuclear stained hepatocytes. Collectively, the presented data indicate that Compound 4d not just stopped the progression of liver cancer but also induced hepatocyte regeneration.

Example 16

Preparation of 4d-Loaded Proniosomes

Preliminary Screening Study

The first step in preparing 4d-loaded proniosomes is selecting the surfactant that could formulate proniosomes that are rehydrated at 25° C. Vesicles formed on hydration of the Span 80-based proniosomes at 25° C., whereas the proniosomes containing Span 60 required a higher temperature (>60° C.) for formation of the vesicles. Therefore, span 80 was selected due to its reasonable hydration temperature acceptable in the clinical setting.

The time of hydration was also considered in choosing the proper conditions for hydration of proniosomes. Table 3 demonstrates that the time of hydration has no significant effect (p>0.05) on % EE. Therefore, 2 min hydration time was chosen because a short hydration time would likely improve patient acceptability.

TABLE 3

Prescreening study for formulation of 4 d-loaded proniosomes

| Formula | Time of hydration (min) | *EE % |
|---|---|---|
| P1 | 2 | 81.94 ± 1.35 |
| P2 | 5 | 82.07 ± 1.79 |
| P3 | 30 | 82.04 ± 1.86 |

Notes:
*the values are expressed as mean ± SD (n = 3), 1 g of carrier per 1 mmole of total lipid mixture, volume of hydration is 10 ml.
EE = entrapment efficiency Fabrication of 4d-Loaded Proniosomes According to $2^3$ Factorial Design Using the Slurry Method 4d-loaded proniosomes were fabricated using the slurry method. Maltodextrin and mannitol were used as the coating carriers. Span 80 was used as the non-ionic surfactant, and CHOL was added as a membrane stabilizer of the nanovesicles (Table 4).

Fabrication of 4d-Loaded Proniosomes According to $2^3$ Factorial Design Using the Slurry Method 4d-loaded proniosomes were fabricated using the slurry method. Maltodextrin and mannitol were used as the coating carriers. Span 80 was used as the non-ionic surfactant, and CHOL was added as a membrane stabilizer of the nanovesicles (Table 4).

TABLE 4

Experimental runs, independent variables and dependent variables in $2^3$ factorial design used for optimization of 4 d-loaded proniosomes

| Formula code | Variables | | | | |
|---|---|---|---|---|---|
| | Independent | | | Dependent | |
| | X1 | X2 | X3 | Y1* | Y2* |
| F1 | −1 | −1 | −1 | 81.94 ± 1.35 | 64.51 ± 1.59 |
| F2 | −1 | −1 | 1 | 71.38 ± 1.24 | 78.92 ± 1.97 |
| F3# | −1 | 1 | −1 | 75.52 ± 1.23 | 87.16 ± 1.78 |
| F4 | −1 | 1 | 1 | 65.64 ± 1.34 | 93.26 ± 1.48 |
| F5 | 1 | −1 | −1 | 82.06 ± 2.31 | 55.87 ± 1.84 |
| F6 | 1 | −1 | 1 | 71.94 ± 1.33 | 71.76 ± 2.32 |
| F7 | 1 | 1 | −1 | 75.92 ± 1.38 | 74.88 ± 1.26 |
| F8 | 1 | 1 | 1 | 65.93 ± 1.29 | 81.78 ± 1.42 |

| Independent variables | Low (−1) | High (+1) |
|---|---|---|
| X1: Type of carrier | Maltodextrin | Mannitol |
| X2: Ratio of Span 80 to CHOL (μmolar ratio) | 140:60 | 160:40 |
| X3: Volume of hydration (ml) | 10 | 15 |

Y1: EE(%),
Y2: $Q_{12\,h}$(%),
*values are mean ± SD (n = 3).
F3# Optimized Formula, 1 g carrier/mmole total lipid mixture.
$Q_{12\,h}$ = drug released after 12 h;
EE = entrapment efficiency;
CHOL = cholesterol

Example 17

Preparation of Niosomes Derived from 4d-Loaded Proniosomes 4d-loaded niosomes were directly formed by hydration of the proniosome powder with distilled water at 25±2° C. Vesicular structures were formed over the carrier surface due to lipid bilayer swelling that transformed with gentle agitation into multilamellar nanovesicles. The multilamellar vesicles are additionally converted by sonication to unilamellar niosomal vesicles.

Example 18

Analysis of $2^3$ Factorial Design

The optimization process was conducted to determine the levels of variables required for manufacturing high quality formulations. A $2^3$ factorial design was used for the optimization of 4d-loaded proniosomes. Three independent variables were selected: Span 80 to CHOL ratio (X1); the carrier type (X2); and the volume of hydration (X3) (Table 5). The selection of the optimized proniosomal formula was based on maximum EE % (Y1) and maximum $Q_{12h}$ (Y2).

It was observed that the values of $R^2$, the predicted $R^2$ and the adjusted $R^2$ for both the EE % (Y1) and $Q_{12h}$ (Y2) were relatively high, suggesting that the data obtained are highly statistically valid (Table 5).

TABLE 5

Output data of the $2^3$ factorial design of 4 d-loaded proniosomes

| Responses | $R^2$ | Adjusted $R^2$ | Predicted $R^2$ | Adequate precision |
|---|---|---|---|---|
| EE % (Y1) | 0.9995 | 0.9992 | 0.9981 | 128.20 |
| $Q_{12\,h}$ (Y2) | 0.9549 | 0.9211 | 0.8197 | 15.52 |

$R^2$ = the coefficient of determination;
$Q_{12\,h}$ = % drug released after 12 h;
EE = entrapment efficiency

Example 19

Comparative Study of the Optimized Proniosomal Formula

Determination of Entrapment Efficiency (EE %)

The EE % of the conventional niosomal formula was found to be 77.06±1.33%. No significant difference (p>0.05) was detected between the optimized proniosomal formula (F3) and the corresponding niosomes.

In Vitro Release Study

Figure 8:
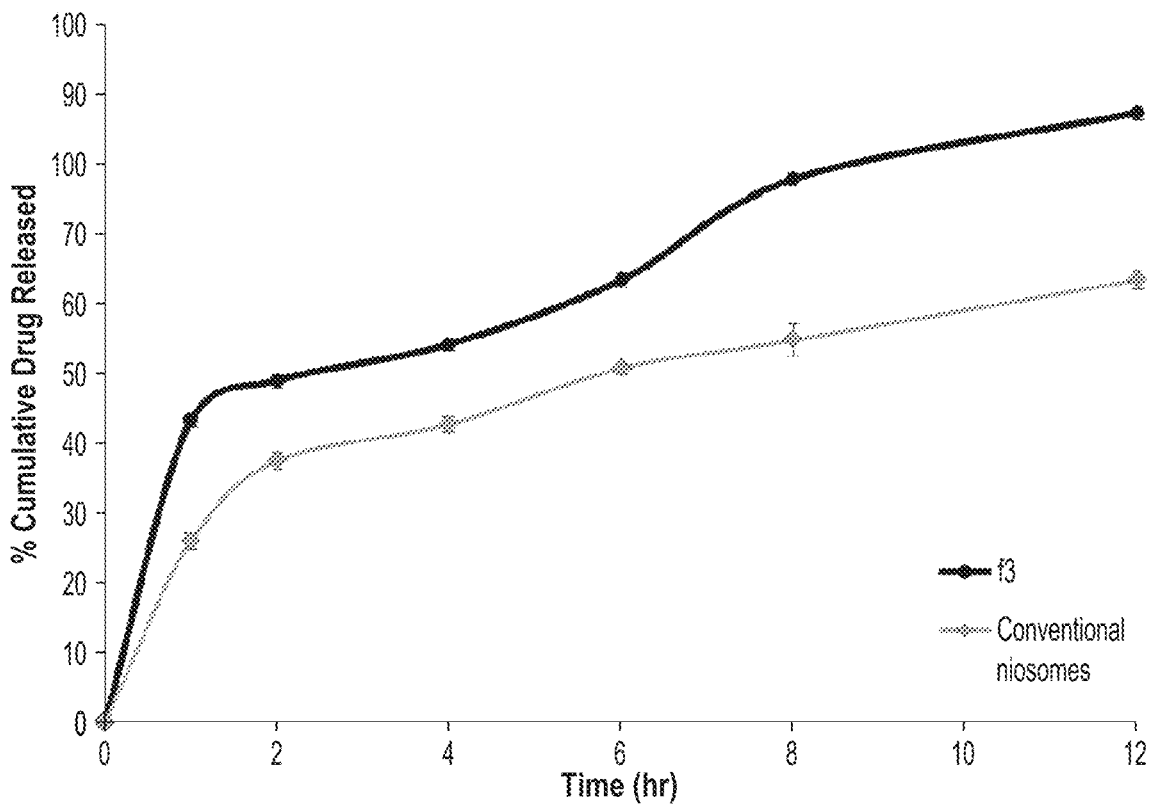
FIG. 8 depicts an in vitro release profile comparing the optimized proniosomal formula and the conventional niosomes.

The in vitro drug release from the optimized proniosomal formula (F3) was compared with that from conventional niosomes. As indicated in FIG. 8, it was found that 4d-loaded proniosomes presented significantly higher cumulative % drug release (p<0.001) than that from the conventional niosomes that achieved 63.36±1.74% cumulative drug released after 12 hours. The release profiles were compared using the similarity factor test. The estimated values of $f_2$ were found to be 34 (less than 50). Therefore, it is obvious that there is a significant difference in the in vitro drug release between the optimized proniosomal formula in comparison to the conventional niosomal formula.

Stability Study

The storage stability of the optimized proniosomal formula and the corresponding niosomal formula was studied for three months at 4-8° C. There was no significant difference in both the drug content and EE % of the stored proniosomal formula (F3) when compared with the fresh proniosomal formula (p>0.05). However, there was a significant decrease in drug content (p<0.01) and EE % (p<0.05) of the fresh niosomal formula when compared to the stored niosomal formula. See Table 6.

TABLE 6

Effect of storage on optimized proniosomal formula and corresponding niosomal formula

| | Proniosomal formula | | Niosomal formula | |
|---|---|---|---|---|
| Parameter | Fresh | Stored | Fresh | Stored |
| Drug content (%) | 98.85 ± 1.45 | 96.63 ± 2.18 | 99.23 ± 1.45 | 91.84 ± 1.79 |
| EE (%) | 75.52 ± 1.23 | 71.33 ± 1.47 | 77.06 ± 1.33%. | 50.13 ± 2.11% |

Notes:
*Each value represents mean ± SD (n = 3), optimized 4 d-loaded proniosomes is F3
Abbreviations: EE, entrapment efficiency Micromeritic Properties It was observed that the angle of repose of 4d-loaded proniosomal powder (34.22°±0.37°) was lower than that of maltodextrin (47.15°±0.48°). Therefore, the flowability of the optimized proniosomal powder (F3) is better than that of maltodextrin powder.

Example 20

Properties of Proniosomal Formula (F3)

Scanning Electron Microscopy (SEM)

Figure 9:
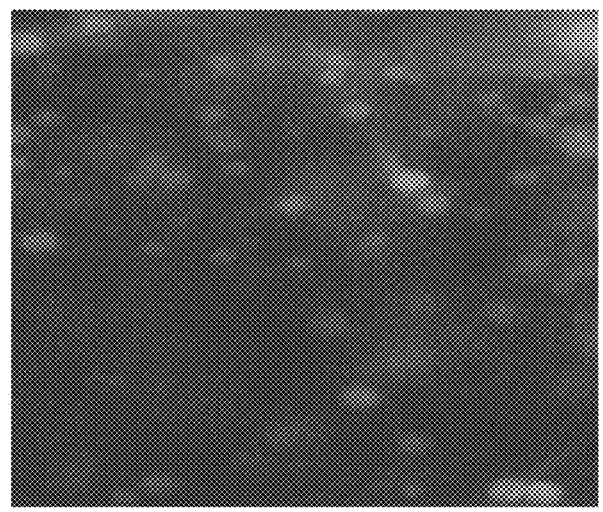
FIG. 9 depicts a scanning electron micrograph of the optimized 4d-loaded proniosomal formula (F3).

The SEM micrograph of the niosomal vesicles formed by hydration of the optimized proniosomal formula (F3) is shown in FIG. 9. The 4d-loaded vesicles appeared as spherical vesicles with sharp boundaries.

Vesicle Size and Zeta Potential Determination

The particle size distribution of the optimized 4d-loaded proniosomal formula (F3) exhibited a unimodal symmetric frequency distribution pattern. The mean vesicle size of the hydrated proniosomal formula was 252.3 nm. Moreover, the polydispersity index (PDI) of F3 was low (0.425) demonstrating a homogenous vesicle size distribution.

The zeta potential is a measure of the net charge of the colloidal dispersion. Large positive or negative zeta potential exhibits the stability of colloidal dispersions due to repulsion between different vesicles that prevents their agglomeration and provides a stable and uniformly distributed suspension. The optimized 4d-loaded proniosomal formula has a high zeta potential value (−25.24 mv) showing that this formula is stable.

Differential Scanning Calorimetry (DSC) Study

Figure 10:
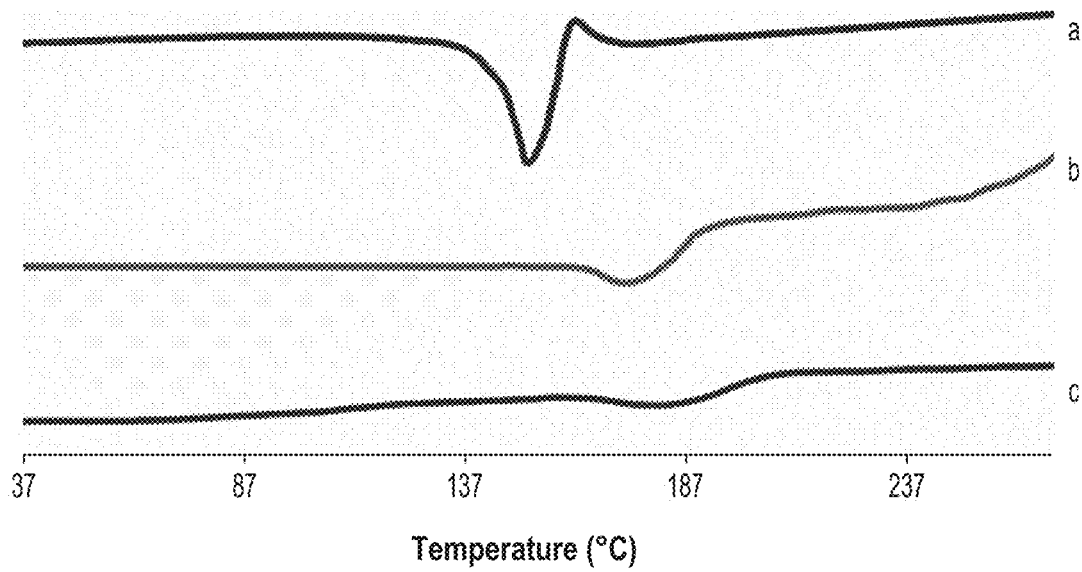
FIG. 10 depicts a DCM thermogram comparison of (a) compound 4d; (b) plain proniosomes; and (c) the optimized 4d-loaded proniosomal formulation (F3).

DSC thermograms of the 4d compound, plain (drug-free) proniosomes, and the proniosomal formula are presented in FIG. 10. The DSC thermogram of 4d showed a sharp endothermic peak at 150° C. which corresponds to its melting point and indicated the crystallinity of 4d. The plain proniosomes demonstrated the appearance of a broad endothermic peak at 172.3° C. The optimized proniosomal formula (F3) exhibited the disappearance of the characteristic endothermic peak of 4d and a shift of the endothermic peak of the lipid bilayer to 181.5° C. (FIG. 10).

Example 21

In Vivo Study of 4d

Thrombocytopenia is considered to be a drawback for the clinical utility of most MDM2-P53 inhibitors. Therefore, the efficacy and safety of the new spirooxindole derivate was investigated in Balb/c mice. The results reveal the safety of both low and high dose of compound 4d in the presented animal model.

A histopathology investigation showed that compound 4d recovered the damaged liver cells and stopped the mitosis (resulting in a lower mitotic index in comparison to untreated mice). This observation may be explained by the ability of compound 4d to stop cell growth at G2/M phase of cancer cells in the in vitro study.

The ability of compound 4d to activate p53 was also evaluated and the immunohistochemistry showed the activated p53 staining in the liver sections. Activated p53 has been linked to the induction of apoptosis and an increase in caspase 3.

The activation of p53 by compound 4d led to higher detection of activated caspase 3 in the liver sections. These data are consistent with the in vitro study where compound 4d killed the cancer cells via the activation of caspase 9 and caspase 8 leading to the activation of caspase 3.

At the same time, the activated p53 increased the level of Ki-67 proliferative marker. Ki-67 is a nuclear protein that is linked to the proliferating cells. Its mRNA level is highly increased during all cell cycle phases even in the quiescent cells. Therefore, it is used as a routine diagnostic marker for tumor cells, in determining the prognosis of the patients. However, Ki-67 is not only linked to cancer proliferation but also its expression is increased after partial hepatectomy.

In the current study, liver dysplasia was reached after treatment of mice with $CCl_4$ leading to the damage of liver cells. Cell proliferation is a biological process in response to different stimuli such as infection of injury. In response to the injection of $CCl_4$ in mice followed by treating these mice with compound 4d, the p53, caspase 3 and Ki-67 were activated and increased in order to stop the proliferation of premalignant cancer cells, and to regenerate the damaged hepatocytes.

Example 22

Prediction of Ligand Efficiency (LE) and Ligand Lipophilic Efficiency (LLE)

Ligand Efficiency (LE) scores:12

LE is used to measure the efficiency of compounds and determine binding affinity (in terms of binding energy or $pIC_{50}$) in relation to the number of heavy atoms in a molecule. This provides a way to compare the affinity of molecules corrected for their size.

LE represents the ratio of the affinity of a ligand divided by the number of heavy (non-hydrogen) atoms in the molecule (LE=ΔG/[number of heavy atoms. LE can be calculated according to the following equation:

$$LE = (pIC_{50} \times 1.37)/NHA$$

where:
$IC_{50}$=half-maximal inhibitory concentration (in term of molar concentration).
NHA=non-hydrogen atom. The recommended LE value for lead-likeness should be in the range of 0.3. The acceptable LE value for drug-likeness should be higher than 0.3.

Table 7 shows LE values of compound 4d equaled 0.2 among all tested cell lines. This means the compound has significant LE.

TABLE 7

Summary of ligand efficiency scores for target compound

|  | NNHA | Clog P (log K) | HCT-116 2 | | | HepG2 0.85 | | | PC-3 1.8 | | |
| --- | --- | --- | --- | --- | --- | --- | --- | --- | --- | --- | --- |
|  |  |  | $pIC_{50}$ | LE | LLE | $IC_{50}$ | LE | LEE | $pIC_{50}$ | LE | LEE |
| Target compound | 37 | 1.19 | 5.69 | 0.21 | 4.5 | 6.07 | 0.22 | 4.88 | 5.74 | 0.21 | 4.55 |

Ligand Lipophilic Efficiency (LLE) 14

Enhancement of compound activity without increasing lipophilicity at the same time is a great challenge. LLE provides a way to estimate the affinity of a compound with respect to its lipophilicity (the difference between the potency and log P). For this reason, LLE is used as a powerful and practical means of keeping lipophilicity under control to avoid any "molecular obesity" during the process of optimization.

LLE can be calculated as follows:

$$LLE = pIC_{50} - C \log P$$

An LLE value≥3 for a lead compound is acceptable, and for a drug candidate LLE value ≥5 is recommended. To get more accurate results, log P was calculated practically, and Log K was measured as indicator and surrogate for log p.

As indicated in Table 8, the target compound's log K=1.19. The LLE values are illustrated in Table 8, demonstrating good LLE values (4.50-4.88). Along with its safety profile (high SI), this compound shows great promise as an anticancer drug.

Example 2³

Comparative Study of the Optimized Proniosomal Formula and the Conventional Niosomes No significant difference in EE % (p>0.05) was detected between the optimized proniosomal formula (F3) and the corresponding niosomes. However, cumulative % drug released of 4d-loaded proniosomes was significantly higher (p<0.001) than that from the corresponding niosomes after 12 h. That may be due to adsorption of the lipid coat of proniosomal vesicles on maltodextrin increasing its effective surface area. Moreover, it could be attributed to enhancement of solubility of 4d and change of its structure from the crystalline to amorphous state in the proniosomal vesicles. In addition, the stability of 4d-loaded proniosomes, after storage for 3 months at 4-8° C., was significantly higher than the corresponding niosomes indicating that proniosomes offer a stable system that could overcome the storage problems associated with conventional niosomes.

It is to be understood that the present teachings are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A spirooxindole nanoformulation including a proniosome loaded with a spirooxindole derivative and sorbitan monooleate as a surfactant, wherein the nanoformulation forms vesicles upon hydration at 25° C.

2. The spirooxindole nanoformulation of claim 1, wherein the spirooxindole derivative comprises.

3. A pharmaceutical composition comprising the spirooxindole nanoformulation of claim 1.

4. The pharmaceutical composition of claim 3, further comprising at least one of maltodextrin and cholesterol.

5. A method of treating cancer comprising administering an effective amount of the pharmaceutical composition of claim 3 to a subject in need thereof that treatment.

6. The method of treating cancer of claim 5, wherein the cancer is hepatocellular carcinoma.

7. A method of preparing the spirooxindole nanoformulation of claim 3, comprising:
- forming a slurry including the spirooxindole derivative, sorbitan monooleate, and cholesterol in an organic solvent; and
- removing the organic solvent from the slurry to produce a proniosomal powder.

\* \* \* \* \*